United States Patent [19]

Middaugh et al.

[11] Patent Number: 5,279,602
[45] Date of Patent: Jan. 18, 1994

[54] SUCTION DRAINAGE INFECTION CONTROL SYSTEM

[75] Inventors: James F. Middaugh, Deerfield; Peter L. Bryant, Lake Forest; Richard W. Grabenkort, Barrington; Timothy J. Oswald, Lincolnshire; Edward S. Tripp, Park City, all of Ill.

[73] Assignee: Abbott Laboratories, Abbott Park, Ill.

[21] Appl. No.: 906,010

[22] Filed: Jun. 26, 1992

Related U.S. Application Data

[63] Continuation of Ser. No. 457,422, Dec. 27, 1989, abandoned, which is a continuation-in-part of Ser. No. 330,552, Mar. 30, 1989, abandoned.

[51] Int. Cl.5 .................................................. A61M 1/00
[52] U.S. Cl. ........................... 604/320; 604/319; 604/321; 604/89; 137/205; 137/432
[58] Field of Search .............................. 604/319-321, 604/310-311, 85-89, 317-318, 322-323, 83-84, 91; 137/205, 208, 432, 433; 141/65

[56] References Cited

U.S. PATENT DOCUMENTS

| | | | |
|---|---|---|---|
| 3,312,221 | 4/1967 | Overment | 604/333 X |
| 3,507,282 | 4/1970 | Burding | 604/333 |
| 3,727,788 | 4/1973 | Holbrook | 604/319 X |
| 3,863,634 | 2/1975 | Reynolds et al. | 604/320 X |
| 3,938,540 | 2/1976 | Holbrook et al. | 137/205 |
| 3,982,538 | 9/1976 | Sharpe | 137/197 X |
| 4,384,580 | 5/1983 | Leviton | 604/319 X |
| 4,396,383 | 8/1983 | Hart | 604/87 X |
| 4,505,703 | 3/1985 | Gale et al. | 604/317 |
| 4,529,398 | 7/1985 | Wong et al. | 604/322 X |
| 4,661,100 | 4/1987 | Rechsteiner | 604/317 X |
| 4,681,571 | 7/1987 | Nehring | 137/205 X |
| 4,693,712 | 9/1987 | Bates | 604/323 |
| 4,855,064 | 8/1989 | Schlein | 604/4 X |

FOREIGN PATENT DOCUMENTS

| | | | |
|---|---|---|---|
| 0941700 | 2/1974 | Canada | 604/321 |
| 8303539 | 10/1983 | PCT Int'l Appl. | 604/85 |
| 8700439 | 1/1987 | PCT Int'l Appl. | 604/319 |

Primary Examiner—Randall L. Green
Assistant Examiner—D. Willse
Attorney, Agent, or Firm—Thomas M. Breininger

[57] ABSTRACT

A suction drainage control system that reduces an operator's exposure to infectious waste by permitting waste-treating material to be dispersed into a sealed chamber in which the infectious waste is contained. The sealed chamber includes a cover with a flexible liner sealed to and suspended therefrom. A reservoir having a closure is provided inside the sealed chamber for storing the waste-treating material, which reservoir is opened by manipulating the flexible liner to remove the closure.

1 Claim, 4 Drawing Sheets

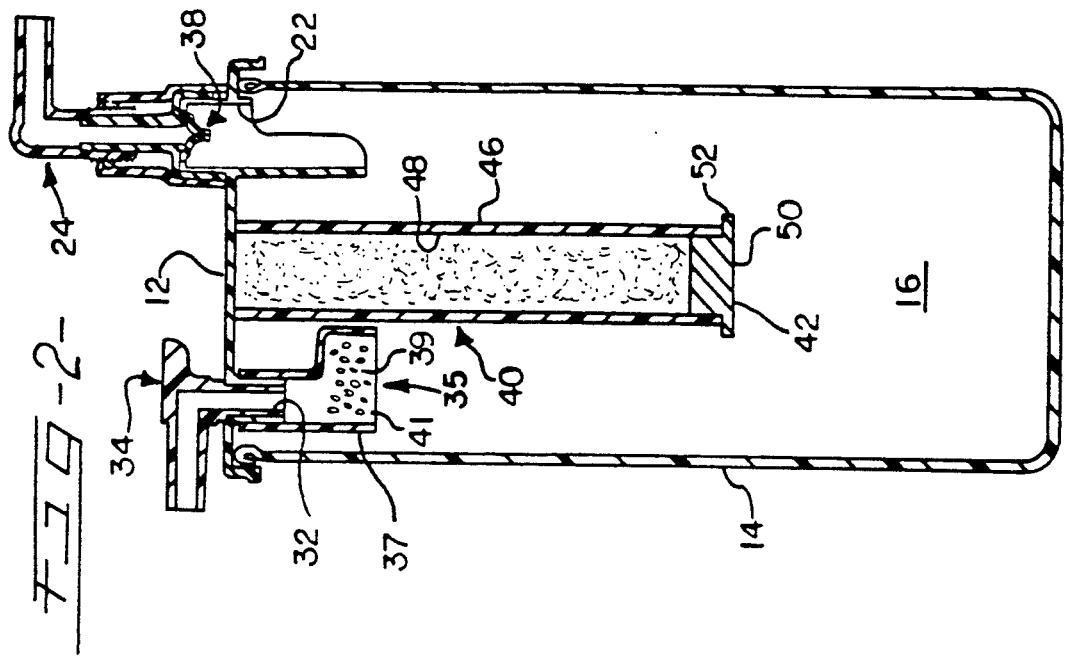
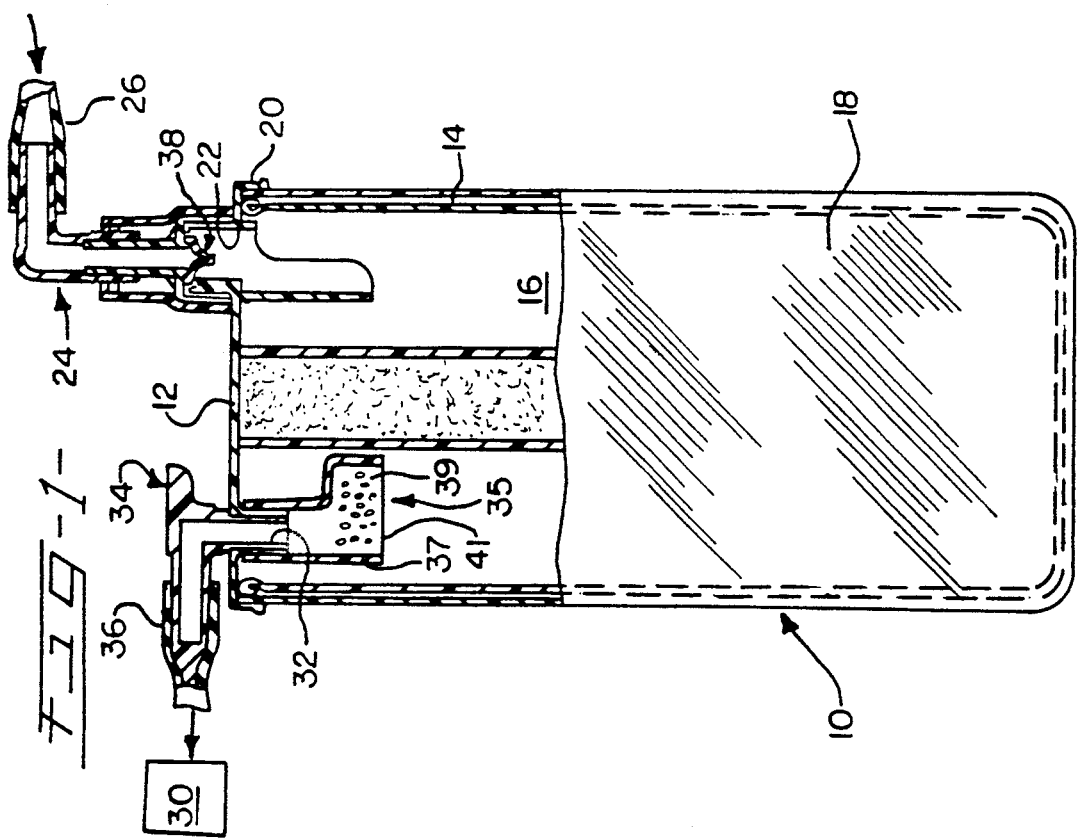

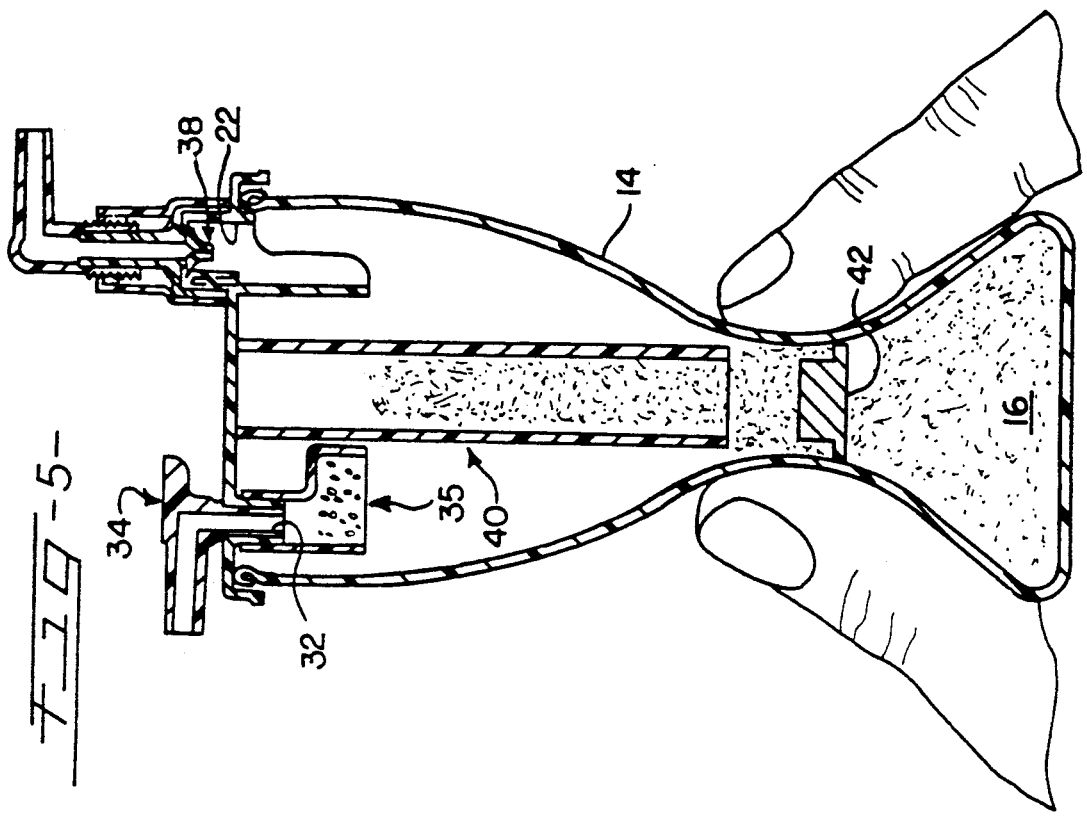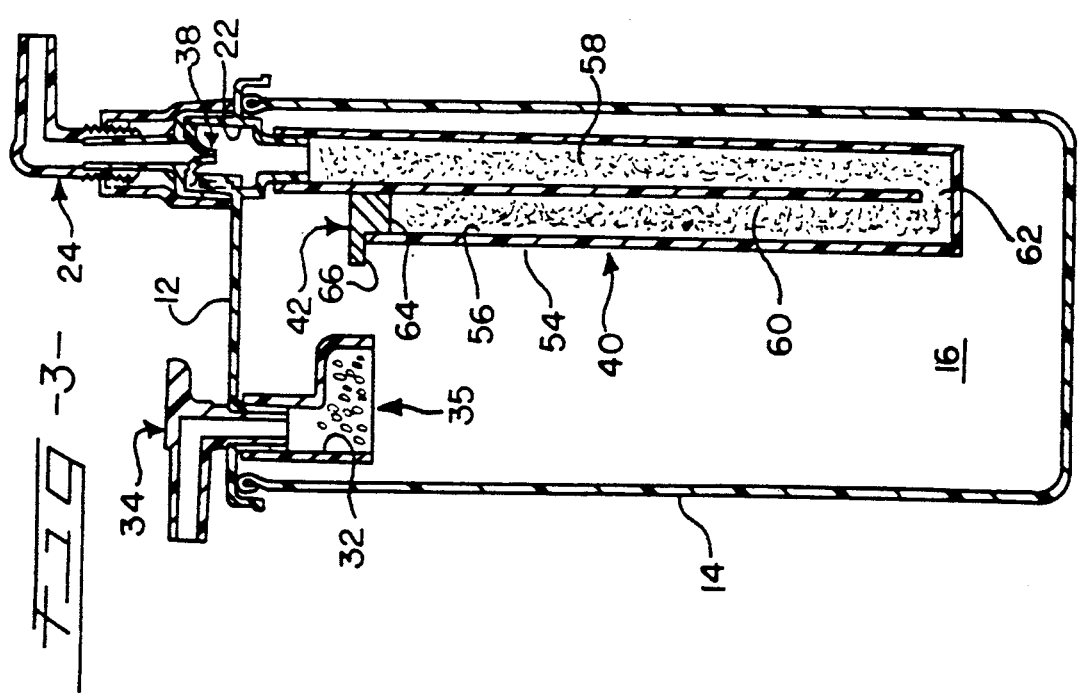

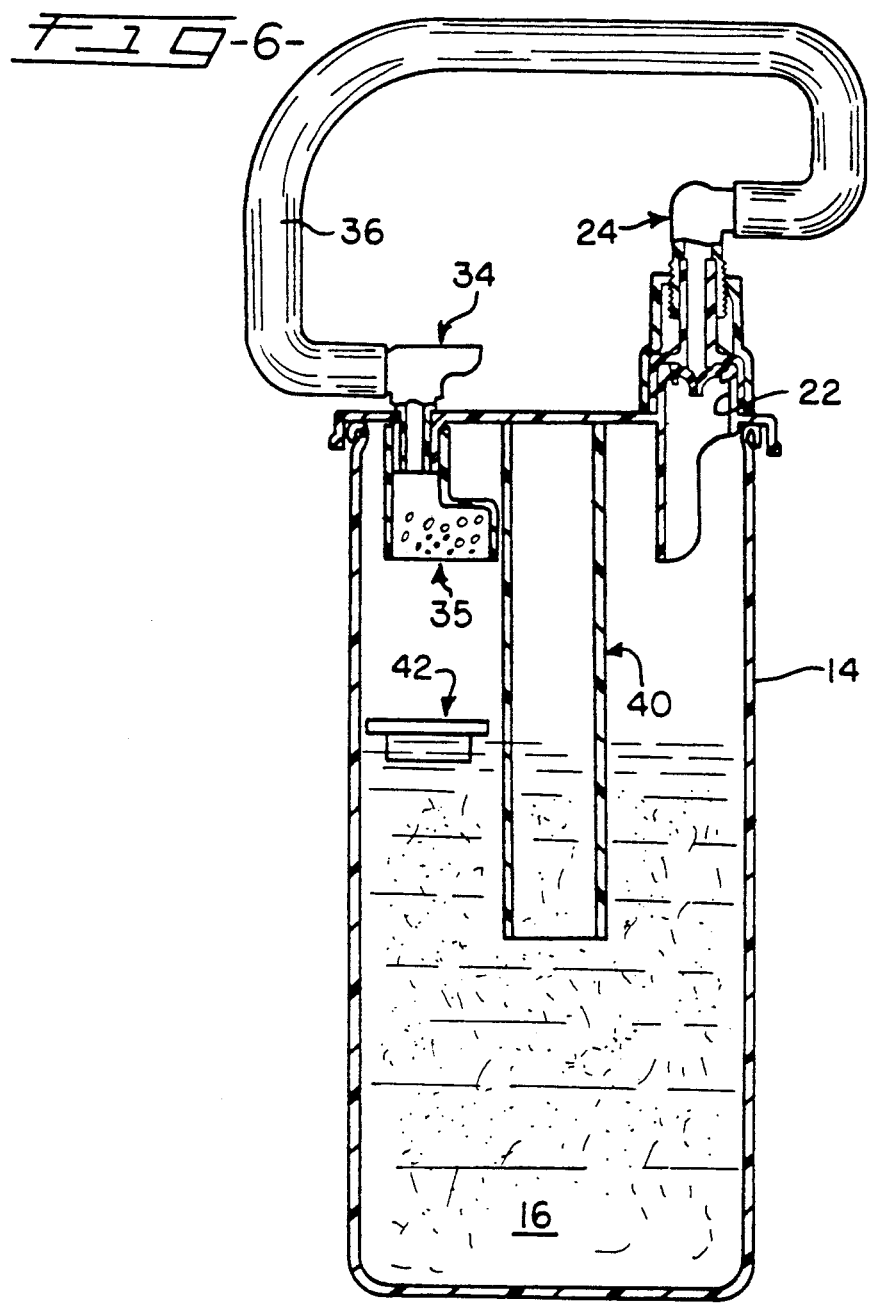
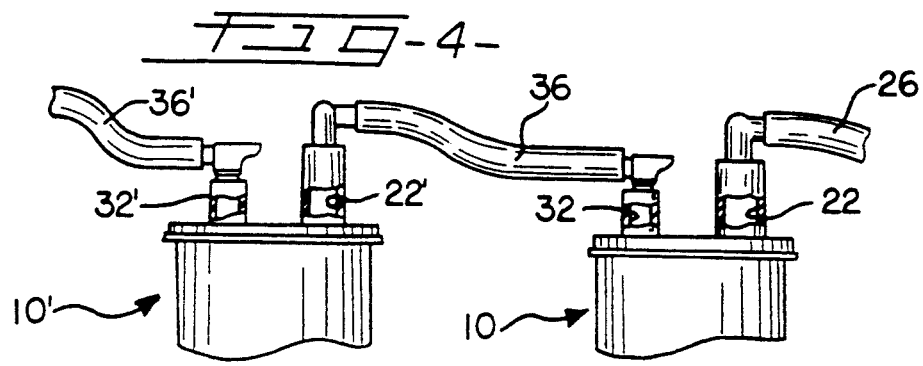

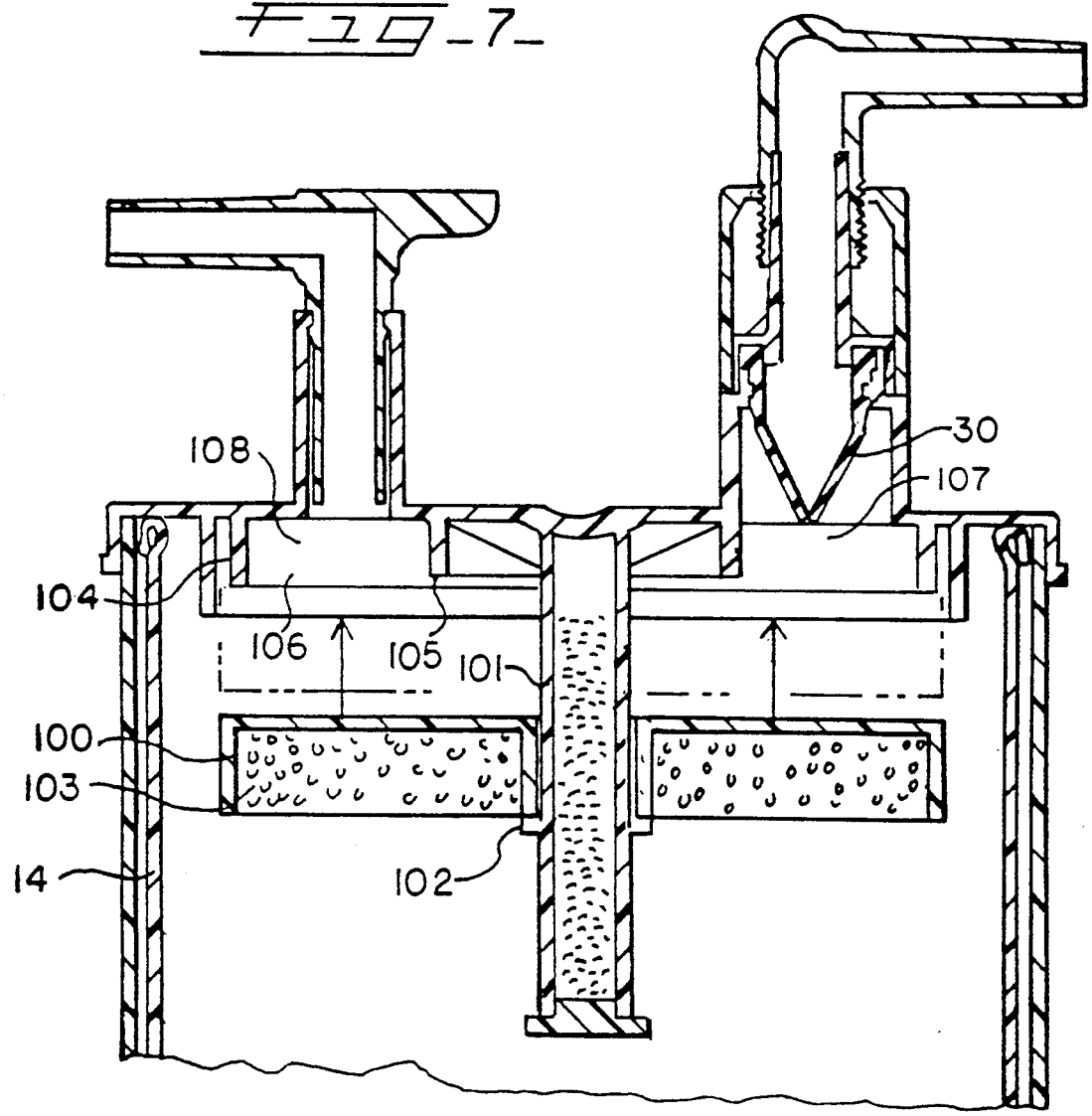

SUCTION DRAINAGE INFECTION CONTROL SYSTEM

CROSS-REFERENCE TO RELATED APPLICATION

This application is a continuation of application Ser. No. 07/457,422, filed Dec. 27, 1989, now abandoned, which is a continuation-in-part of application Ser. No. 07/330,552, filed Mar. 30, 1989, now abandoned.

BACKGROUND OF THE INVENTION

Suction drainage systems having a connection from a rigid container or a flexible liner to the body of a patient and a connection from the container or liner to a suction source have been widely utilized in hospitals. These systems collect waste from surgical and other patients in a disposable container or flexible liner having an integral lid or cover. The waste being collected often is highly infectious and often subject to exposure caused by spills or a failure of the suction drainage system.

Accordingly, it is an object of the present invention to provide a suction drainage container infection control system.

It is a further object of the present invention to provide a suction drainage infection control system incorporating an enclosed reservoir containing a waste treating material, such as a germicide and/or absorbent disposed within a reservoir that can be opened to empty its contents when desired and/or improved valves and/or a transfer system and/or locking features in the lid to minimize the escape of fluid after capture.

SUMMARY OF THE INVENTION

The present invention is directed to a suction drainage infection control system.

More particularly, the present invention is directed to a suction drainage infection control system that incorporates a germicide and/or an absorbent in a flexible and sealed liner or bag in which infectious or contaminated waste is collected. The waste-treating material is disposed in a stoppered reservoir in the sealed liner. The reservoir is opened by manipulating the stopper through the liner.

This invention is also directed to a suction drainage infection control system having improved valves, a multi-container transfer system and locking features in the lid of the rigid container or flexible liner.

The suction drainage infection control system of the present invention can include means for chemically treating the waste and/or means for capturing and transferring the waste in a solid or semi-solid state. Each suction drainage canister may be used alone or in series with one or more additional canisters.

The suction drainage infection control system of the present invention minimizes the risk of exposure for hospital personnel to infectious waste by decreasing the risk of infection and spills caused by failure to cap off full or partially full waste containers, accidental cap disconnection and liner breakage.

The suction drainage infection control system of the present invention promotes the safe handling of potentially infectious suction waste by exposing the collected waste to an effective germicidal agent that is capable of killing many types of bacteria and viruses at room temperature. The germicide is effective against HIV, hepatitis B, herpes simplex I, polio, adeno virus, and many other potentially infectious materials, and thus dramatically reduces the potential of cross-contamination between patients and minimizes the associated risk to health care workers.

Other advantages and features of the present invention will become apparent from the following detailed description, the accompanying drawings, and the appended claims.

BRIEF DESCRIPTION OF THE DRAWINGS

FIG. 1 is an elevational view, partly in section, illustrating an embodiment of the present invention;

FIG. 2 is a cross-sectional illustration of one embodiment embodying principles of this invention;

FIG. 3 is a vertical cross-sectional illustration of another embodiment of the present invention;

FIG. 4 is a fragmentary diagrammatic view of two systems connected in series;

FIG. 5 is a schematic illustration showing activation of the embodiment of FIG. 2 of the present invention;

FIG. 6 is a view substantially similar to FIG. 2 after the sealed chamber is filled and having inlet and outlet ports of the sealed chamber closed; and FIG. 7 is a fragmentary vertical section of an embodiment of the present invention that is adapted for use with two or more systems connected in series.

DETAILED DESCRIPTION OF THE PREFERRED EMBODIMENTS

While the present invention is susceptible of embodiment in many forms, there is shown in the drawings and will hereinafter be described two presently preferred embodiments with the understanding that the present specification sets forth exemplifications of the invention, which are not intended to limit the invention to the specific embodiments illustrated.

Referring to the drawings, FIG. 1 is a vertical section of a first embodiment of the suction drainage infection control system 10 of the present invention. The system 10 includes a cover 12 and a flexible bag or liner 14. Cover 12 and liner 14 define a sealed chamber 16 in which waste is collected. The system 10 may further include a canister 18 the open end of which is enclosed by the cover 12 in air-tight engagement therewith.

Cover 12 may be formed from a rigid plastic material and is supported by canister 18. As illustrated, liner 14 is suspended from the underside of cover 12. The upper end of liner 14 is fused or sealed to the underside of cover 12 in a completely air tight manner. Liner 14 is preferably made of substantially transparent rubber-like material or thermoplastic material.

As illustrated, canister 18 surrounds the liner 14 in a protective manner and is rotatably secured to a skirt portion 20 provided on cover 12. Canister 18 may be made of relatively rigid plastic material and is closed at its bottom end. Normally, canister 18 itself does not become contaminated by waste which may be highly infectious or even contagious, so it may be repeatedly used without sterilization each time a system 10 is used. In a preferred form, canister 18 has a cylindrical shape although its shape is not critical. FIG. 1 is an illustration of an embodiment of the invention prior to emptying the waste treating material into the sealed chamber 16.

As illustrated in FIG. 1, cover 12 includes an inlet port 22 which is connected to a hollow inlet fitting 24, projecting upwardly from cover 12, and which is, in turn, connected to an inlet line or tube 26.

Cover 12 further includes an outlet port 32 which is connected to a hollow outlet fitting 34, projecting upwardly from cover 12 and which is, in turn, connected to an outlet tube or line 36 that is connected to a suction source 30.

A nonmechanical valve 35 is mounted in the lid 12. The nonmechanical valve 35 comprises a housing 37 that contains a polyethylene foam 39 containing swellable moisture-sensitive particles 41 made of polymers or other suitable materials. A suitable nonmechanical valve is disclosed in published PCT Application No. WO 87/00439. This valve permits normal air flow through suction opening 34 until it becomes wet, whereupon the polymer particles swell to block air and waste flow.

A valve 38 is provided in the flow path leading from the inlet line 26 to the sealed chamber 16. Valve 38 allows for one-way flow of waste from the source to be drained to the sealed chamber 16. A one-way double slit "duck bill" valve which prevents a reverse flow of material through the inlet port 22 is one example of a means for preventing escape of waste from the sealed chamber 16. Other suitable duck bill valves are disclosed in U.S. Pat. Nos. 3,822,720 and 3,901,272.

As shown in FIG. 2, the sealed chamber 16 wholly encloses a normally closed reservoir generally indicated by reference numeral 40, which contains a waste-treating material while the reservoir 40 remains closed. A closure 42 maintains the closed condition of the reservoir 40 as long as it is secured in the open end thereof.

When the reservoir 40 is opened, by removal of closure 42, the waste-treating material is dispersed into the sealed chamber 16. As used herein, the terms "dispersed" or "dispersion" are meant to include the release of waste-treating material into the sealed chamber 16.

The waste-treating material may be in the form of a powder or liquid (single or multi-component) disinfectant and preferably comprises a germicide and/or an absorbent. The germicide and/or absorbent will treat contaminants contained in the waste. In a preferred embodiment, the absorbent is of a type that will swell in size upon dispersion into the waste.

Representative suitable germicides include calcium hypochlorite, chlorinated trisodium phosphate, N-chlorosuccinimide, 1,3-dichloro-5,5-dimethylhydantoin, potassium dichloro-s-triazinetrione, sodium benzenesulfonchloramide, sodium hypochlorite, sodium p-toluenesulfonchloramide, sodium dichloroisocyanurate, dihydrate, sodium dichloro-s-triazinetrione, p-sulfondichlor-amidobenzoic acid, p-toluenesulfondichloramide, trichloroisocyanuric acid, trichloromelamine, alcohols, formaldehyde, glutaraldehyde, hydrogen peroxide, iodines, quaternary ammonium compounds, paraacetic acid, paraformaldehyde, and phenols. Preferred germicides include 1,3-dichloro-5,5-dimethylhydantoin, potassium dichloro-s-triazinetrione, N-chlorosuccinimide, and sodium dichloroisocyanurate dihydrate.

Representative suitable absorbents include cellulose fibers, cross-linked polymeric salts, diatomaceous earth, dried clay, expanded silicate particulates, ground corncobs, perlite, silica gel, shredded polypropylene microfibers, sodium/calcium borosilicate glass, starch grafted sodium polyacrylate, thermally reticulated polyether polyurethane, and vermiculite.

In the embodiment illustrated in FIG. 2, the reservoir 40 for storing the waste-treating material is an elongated and open-ended tube 46 which depends from and has its upper end suitably sealed to the underside of cover 12. Tube 46 is preferably comprised of a flexible plastic material and defines a cavity 48 which is open at its lower end. The flexibility of tube 46 allows it to be configured in arrangements other than that illustrated in FIG. 2. Alternatively, reservoir 40 could be formed as a bag or from a rigid material which is appropriately configured.

In the embodiment illustrated in FIG. 2, the closure 42 is a plug 50 that is releasably secured at the open-bottom end of the tube 46 to contain the waste-treating material within the cavity 48. Plug 50 is provided with a lip 52 which facilitates removal of the plug 50 from the tube 46. Plug 50 is preferably formed from a low-density material such as cork or a buoyant rubber material which permits it to float in the waste contained in sealed chamber 16. The ability of the plug 50 to float provides a visual indication that the system has been activated and the waste-treating material has been dispersed in the sealed chamber 16.

Another embodiment of the present invention is illustrated in FIG. 3. The embodiment illustrated in FIG. 3 is comprised of many of the same components as the embodiment illustrated in FIGS. 1 and 2. Accordingly, those components which function similarly to those illustrated in FIG. 2 have been identified by like reference numerals in FIG. 3.

In the embodiment illustrated in FIG. 3, reservoir 40 is an elongated and open-ended tube 54 defining a cavity 56 having a generally U-shaped configuration. As illustrated, tube 54 is arranged in series with the first flow path leading to the sealed chamber 16 of the system 10. Tube 54 defines an open-ended descending leg section 58, an open-ended ascending leg section 60, and an elbow section 62 which joins leg sections 58 and 60.

As illustrated, the open end of descending leg section 58 is suitably secured to the inlet port 22 beneath valve 38. The open end of the ascending leg section 60 is raised or elevated from a lower or bottom end of the sealed chamber 16 so as to prevent back syphoning and bridging. Although illustrated in a U-shaped configuration, it will be appreciated that the tubing 54 may assume different configurations other than that illustrated without detracting from the essence of the present invention.

In the embodiment illustrated in FIG. 3, the closure 42 is defined by a plug 64 which is releasably secured at the open end of the ascending leg section 60. Plug 64 is provided with a lip 66 which facilitates removal of the plug 64 from the tube 54. Plug 64 is preferably formed from a low-density cork material or a buoyant rubber material which permits it to float in the waste received in the sealed chamber 16. The ability of the plug 64 to float provides a visual indicator that the system has been activated.

As schematically illustrated in FIG. 4, two systems 10 and 10' may be arranged in series relative to each other between the suction source and the source from which waste is to be drawn. Preferably, in such an arrangement, the systems 10 and 10' are substantially similar to each other. Therefore, similar component parts of the canister assemblies are represented by "prime" reference numerals in FIG. 4. In such arrangement, the outlet tube 36' of system 10' is connected to a source of suction or negative pressure. The outlet tube 36 extending from outlet port 32 of system 10 is connected to inlet port 22' of system 10'. The inlet port 22 of system 10 extends, via inlet tube 26, to the source of waste. It should be noted that the embodiment shown in FIG. 3 cannot be connected in series.

FIG. 7 is a fragmentary vertical section of an embodiment of the present invention that is adapted for use with two or more canisters connected in series as shown in FIG. 7. In this embodiment, a float 100 is slidably mounted on post 101, which has a knob 102 at its lowermost portion to support the float in its lowermost position. The float 100 is packed with buoyant material 103 so that when the waste reaches a level in the liner 14 where it contacts the lower surface of the buoyant material 103 the float 100 rises until circular wall 104 is contacted by the upper surface of the float 100. Circular wall 104 forms with circular wall 105, an annular channel 106 through which opening 107 communicates with opening 108. The float 100 thus prevents the flow of waste into the liner 14. However, as seen from the drawings, suction is present and continues to draw in waste through valve 30. As a result of the suction, the waste will flow directly from inlet opening 107 to outlet opening 108 through circular channel 106. As shown in FIG. 4, waste then can pass from one canister to another. This feature is referred to as the transfer system.

As will be appreciated from FIG. 5, dispersion or release of the waste-treating material into the sealed chamber 16 may be simply effected by having an operator collapse the liner 14 and remove the closure 42 from the reservoir 40. The provision of a lip on the closure member facilitates removal of the closure member from the end of the reservoir. After closure 42 is removed from the reservoir, the cover 12 and liner 14 are disposed in the canister 18.

In the embodiment illustrated in FIG. 5, removal of the closure 42 from the open end of the reservoir 40 allows the waste-treating material to freely fall or dispense into the sealed chamber 16. Because the closure 42 is preferably comprised of a low-density material, it will tend to float in the waste thereby providing a visual indication that the system has been activated as shown in FIG. 6.

During operation, a negative pressure or suction is introduced into the sealed chamber 16 as by connecting the vacuum or suction line 36 extending from the vacuum source 30 to the outlet port 32. When suction or negative pressure is created in the sealed chamber 16, a positive pressure differential is developed on opposite sides of valve 38. The suction or negative pressure created draws waste through the inlet port 22 in a manner forcing an expansion of the valve 38 to permit flow therethrough into the sealed chamber 16 wherein the waste is received and collected. The positive pressure differential allows the valve 38 to act as a one-way flow valve.

In the embodiment illustrated in FIG. 3, the reservoir 40 is arranged in series with the inlet port 22 of the waste receptacle. After the closure 42 has been removed from the reservoir and waste flows from the waste source, the waste will be caused to pass through the reservoir 40 thereby forcibly and automatically dispensing the waste-treating material contained in the tube 54 into the sealed chamber 16. When the chamber 16 is filled, the nonmechanical valve closes off port 37 when the polymer particles 33 disposed therein swell to block air and waste flow.

Operation of the suction system of the present invention may be stopped at any desired time by disconnecting the suction source 30 from the outlet port 32 of the waste receptacle. Advantageously, since the liner 14 is sealed to cover 12, once the liner is filled, the cover 12 and liner 14 may be removed from the canister 18 and disposed of intact.

After the operation of the suction system is stopped or halted, the inlet tube 26 is disconnected from the inlet fitting 24. As illustrated in FIG. 6, tube 37 may then be placed over the inlet fitting 24 and outlet fitting 34 such that the inlet and outlet ports 22, 32, respectively, are closed and the cover 12 and liner 14 may be lifted out of the canister 18 and disposed of along with its drainage content. As will be understood, it is a simple expedient to reconnect a new canister cover and liner to a suction source.

From the foregoing, it will be observed that numerous modifications and variations can be effected without departing from the true spirit and scope of the novel concept of the present invention. It will be appreciated that the present disclosure is intended to set forth exemplifications of the invention which are not intended to limit the invention to the specific embodiments illustrated. The disclosure is intended to cover by the appended claims all such modifications as fall within the scope of the claims:

What is claimed is:

1. A suction system for draining and treating waste from a source, said suction system comprising:
  a sealed chamber including a flexible liner for receiving waste from said source including a cover having waste inlet means and outlet means in sealing engagement therewith;
  a reservoir attached to said cover and wholly enclosed within said sealed chamber for storing waste-treating material;
  removable closure means for closing said reservoir until the flexible liner is manipulated to remove the closure from the reservoir prior to sealing of said cover to said chamber so as to permit dispersion of the waste-treating material into the sealed chamber prior to recepror waste therein; and
  means in said cover attached to a suction source, sealing-means in said system to seal suction from collected waste in the container when the waste in the container has reached a specified level and transfer the suction and waste flow to additional containers that are connected thereto, said sealing-means comprising a float in the container that is movably mounted to the cover, said cover and float being constructed and arranged to close off the suction and inlet means from the container when it reaches the specified level, but permit flow between said suction and inlet means.

* * * * *

UNITED STATES PATENT AND TRADEMARK OFFICE
CERTIFICATE OF CORRECTION

PATENT NO. : 5,279,602
DATED : January 18, 1994
INVENTOR(S) : James F. Middaugh; Peter L. Bryant; Richard W. Grabenkort; Timothy J. Oswald; Edward S. Tripp It is certified that error appears in the above-indentified patent and that said Letters Patent is hereby corrected as shown below:

Column 6, line 47: Replace "recepror" with --receipt of--

Signed and Sealed this

Twenty-sixth Day of July, 1994

Attest:

BRUCE LEHMAN

*Attesting Officer*   *Commissioner of Patents and Trademarks*